US008367631B2

(12) United States Patent
Pitard

(10) Patent No.: US 8,367,631 B2
(45) Date of Patent: *Feb. 5, 2013

(54) PHARMACEUTICAL COMPOSITION WHICH IMPROVES IN VIVO GENE TRANSFER

(75) Inventor: Bruno Pitard, Reze (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/659,618

(22) Filed: Mar. 15, 2010

(65) Prior Publication Data

US 2010/0179212 A1    Jul. 15, 2010

Related U.S. Application Data

(63) Continuation of application No. 10/502,973, filed as application No. PCT/FR03/00407 on Feb. 7, 2003, now Pat. No. 7,709,452.

(51) Int. Cl.
| | |
|---|---|
| A61K 48/00 | (2006.01) |
| A01N 63/00 | (2006.01) |
| A01N 65/00 | (2009.01) |
| C12N 5/00 | (2006.01) |
| C12N 5/02 | (2006.01) |
| C07H 21/02 | (2006.01) |
| C07H 21/04 | (2006.01) |

(52) U.S. Cl. .................................................. 514/44 R
(58) Field of Classification Search .......................... None
See application file for complete search history.

(56) References Cited

U.S. PATENT DOCUMENTS

| | | | | |
|---|---|---|---|---|
| 5,792,475 | A | * | 8/1998 | Davis et al. .................... 424/489 |
| 6,221,959 | B1 | | 4/2001 | Kabanov et al. |

FOREIGN PATENT DOCUMENTS

| | | |
|---|---|---|
| WO | WO 93/15745 | 8/1993 |
| WO | WO 96/15778 | 5/1996 |
| WO | WO 96/21470 | 7/1996 |
| WO | WO 99/31262 | 6/1999 |
| WO | WO 00/47186 | 8/2000 |
| WO | WO 00/51645 | 9/2000 |
| WO | WO 01/08709 A1 | 2/2001 |
| WO | WO 01/60415 A1 | 8/2001 |
| WO | WO 01/05911 A2 | 9/2001 |
| WO | WO 02/061040 A2 | 8/2002 |

OTHER PUBLICATIONS

Mary C. Phelan (May 1, 2006 Online) "Techniques for Mammalian Cell Tissue Culture", Current Protocols in Cytometry, Publisher Wiley & Sons, NY., NY, Supplement 36, Appendix 3B, pp. 1-18.*
http://www.sigmaaldrich.com/etc/medialib/docs/Sigma/Product_Information_Sheet/1/t2145pis.Par.0001.File.tmp/t2145pis.pdf.*
http://www.google.com/#q=tyrode%27s+medium+culture&hl=en&prmdo=1&prmd=ivns&sa=X&ei=ixp-TsW0GcrG0AG-1vn7Dw&ved=0CBYQpwUoBg&source=Int&tbs=cdr:1%2Ccd_min%3A1%2F1%2F1900%2Ccd_max%3A2%2F7%2F2002&tbm=&fp=1&biw=1181&bih=862&bav=on.2,or.r_gc.r_pw.&cad=b.*
Prockop, et al. (2001) "Maximizing the In Vivo Efficiency of Gene Transfer by Means of Nonviral Polymeric Gene Delivery Vehicles", Journal of Pharmaceutical Sciences, 91(1): 67-76.*
Klebe et al., "Uptake by Cells of Nucleic Acids Promoted by Compounds Sharing the Pleiotropic Effects of Poly(Ethylene Glycol)," XP 000572777, Alan R. Liss, Inc., pp. 245-250; 1986.
Prokop et al., "Maximizing the In Vivo Efficiency of Gene Transfer by Means of Nonviral Polymeric Gene Delivery Vehicles," XP-002253712, Journal of Pharmaceutical Sciences, vol. 91, No. 1, pp. 67-76, Jan. 2002.
Kakizawa et al., "Block copolymer micelles for delivery of gene and related compounds," Advanced Drug Delivery Reviews, vol. 54, pp. 203-222, 2002.
Hanecak et al., "Antisense Oligonucleotide Inhibition of Hepatitis C Virus Gene Expression in Transformed Hepatocytes," Journal of Virology, vol. 70, No. 8, pp. 5203-5212, Aug. 1996.
Locke et al:, "Tyrodes Solution," www.whonamedit.com, Gibco, Chapt. 1, p. 39, Oct. 30, 2006.
Caplen et al., "Specific Inhibition of Gene Expression by Small Double-Straded RNAs in Invertebrate and Vertebrate Systems," Proc. Natl. Acad. Sci., vol. 98, No. 17, pp. 9742-9747, Aug. 14, 2001.
Subramanian et al., "Differentiation Potential of Intestinal Mesenchyme and its Interaction with Epithelial Cells: A Study Using β-Galactosidase-Expressing Fibroblast Lines," Cell Biology International, vol. 25, No. 8, pp. 741-751, 2001.

*Primary Examiner* — Robert M Kelly
(74) *Attorney, Agent, or Firm* — Oliff & Berridge, PLC

(57) ABSTRACT

A pharmaceutical composition, including at least one nucleic acid, a Tyrode's medium having 140 mM NaC1, 6 mM KC1, 3 mM CaCl$_2$, 2 mM MgCl$_2$, 10 mM Hepes, pH 7.4, and 10 mM glucose; and a tetrafunctional copolymer of formula (I):

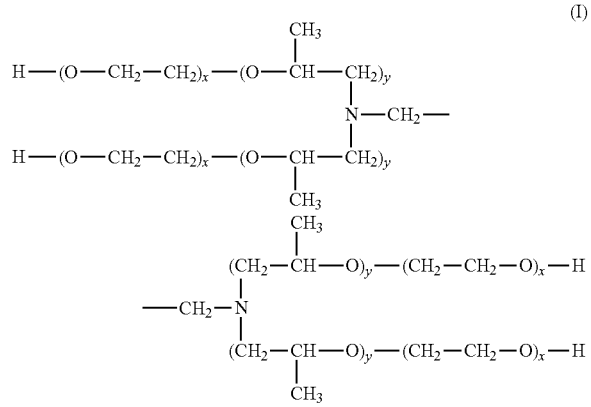

Figure 1:
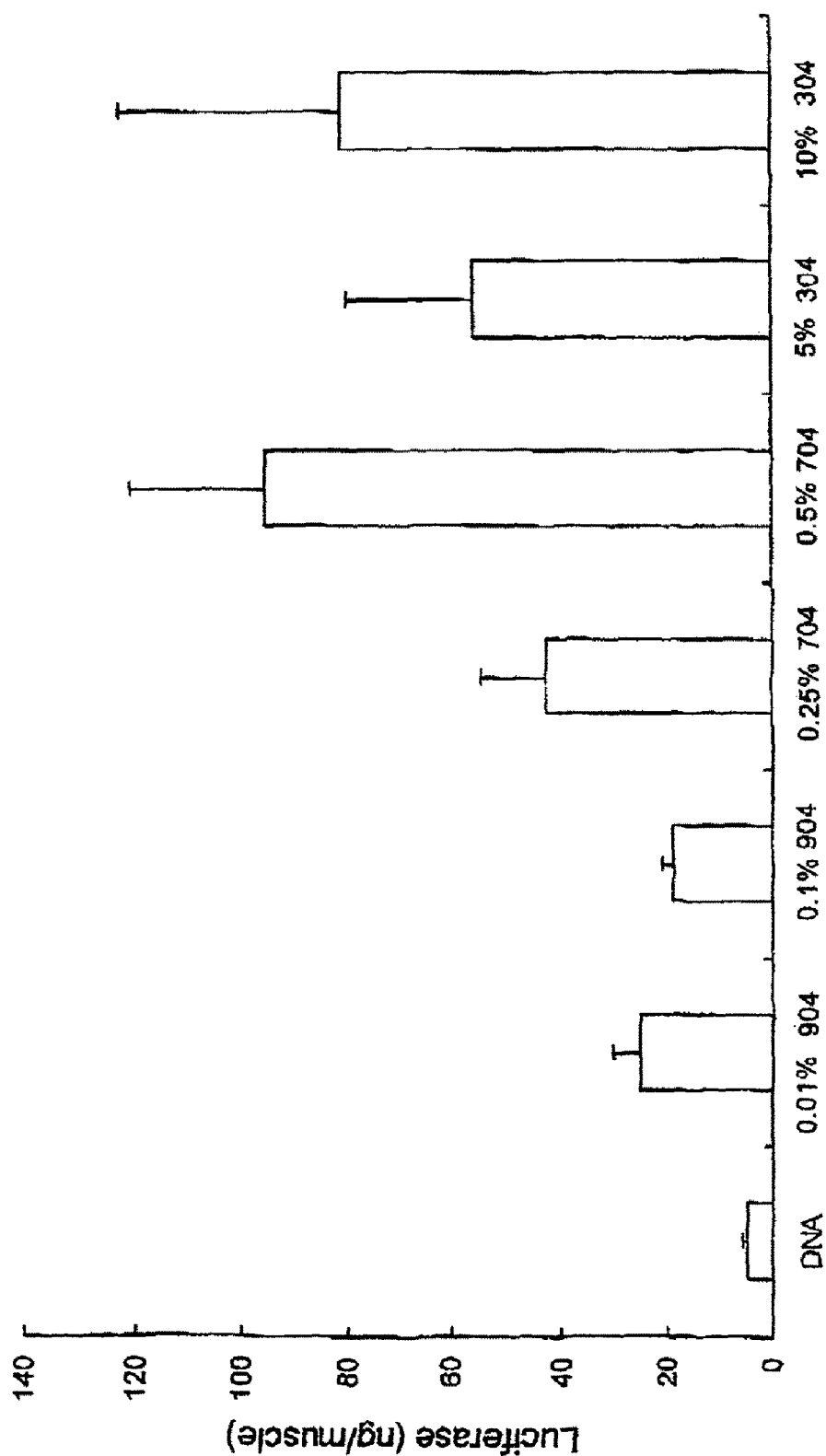

where x and y represent, independently of one another, an integer of between 1 and 500, the tetrafunctional copolymer is in a form of a mineral salt wherein said tetrafunctional copolymer is in a cationic form. The compound of formula (I) has a molecular weight of between 1,000 and 25,000 g/mol and an EO/PO ratio of 0.8 to 1.2.

10 Claims, 5 Drawing Sheets

A: naked DNA
B: 5% 304
C: 10% 304
D: 0.01% 904
E: 0.1% 904

A: naked DNA; B: 5% 304; C: 0.25% 704; D: 0.1% 904; E: $10^{-3}$% 908

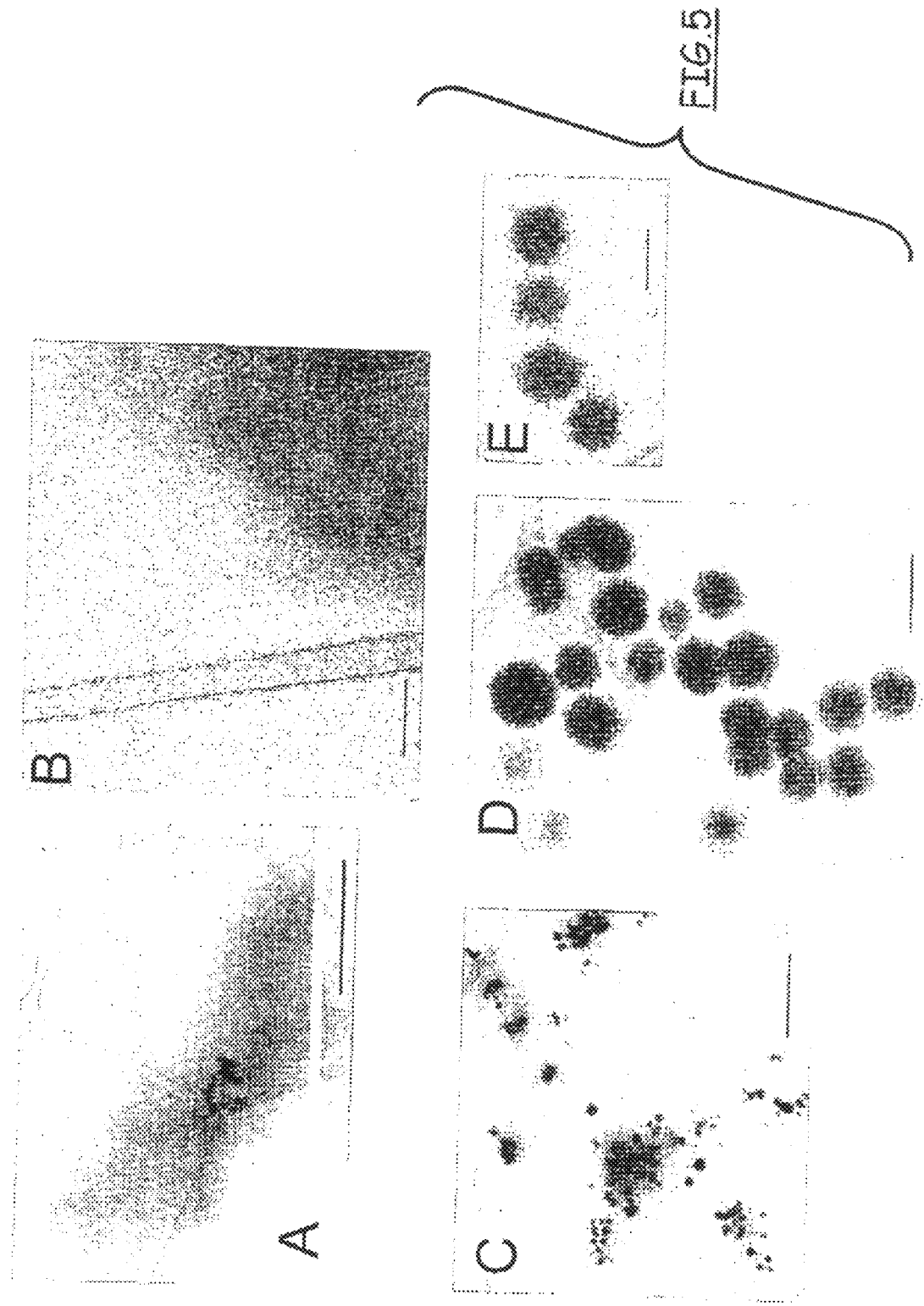

PHARMACEUTICAL COMPOSITION WHICH IMPROVES IN VIVO GENE TRANSFER

This is a Continuation of application Ser. No. 10/502,973 filed Mar. 8, 2005, now issued as U.S. Pat. No. 7,709,452, which is a National Stage Application of PCT/FR03/00407 filed Feb. 7, 2003. The entire disclosure of the prior applications are hereby incorporated by reference in their entirety.

The present invention is directed, in a main capacity, toward a pharmaceutical composition for facilitating the cellular transfer of nucleic acid(s) and more particularly into muscle or cardiac cells in vivo.

The problem under consideration in the context of the present invention is that of the transfer of gene information into a cell, and more particularly into its nucleus, in order for the gene under consideration to be translated therein into protein.

Currently, two technologies are mainly used for cellular gene transfer. The first uses adeno-associated virus, AAV, which is a recombinant virus. As regards the second, it is electrotransfer, which consists in imposing an electric field on the cells under consideration, after having injected the DNA into them. Although these two methods make it possible to obtain satisfactory levels of gene transfer efficiency, they have, on the other hand, a disadvantage in terms of toxicity. What is more, AAV today raises many technical difficulties in terms of its preparation, purification and/or characterization, and the potential risk of integration into the host cell's genome could bring about cancerization phenomena. Finally, gene transfer into the cardiac muscle cannot be obtained by means of the electrotransfer technique for survival reasons.

In this case, the present invention is precisely advantageous for transfection into skeletal, smooth and cardiac muscle cells.

As regards synthetic vectors, like cationic lipids for example, they prove to be inefficient in vivo. Only naked DNA is capable of resulting in the expression of a protein after injection into skeletal and cardiac muscle. Unfortunately, the amount of protein synthesized after intramuscular injection of naked DNA remains insufficient to envision clinical applications. In fact, one of the major problems of using naked DNA for gene transfer into muscle tissues is its poor efficiency, which is not improved by increasing amounts of injected DNA. Now, for reasons of convenience, in particular in terms of accessibility, it would be particularly advantageous to favor the expression of proteins of local or systemic therapeutic interest in these muscles.

Consequently, there exists today a real need for a vector that is ideal in gene therapy, i.e. a nontoxic vector which does not induce an immune reaction and which makes it possible to obtain optimal expression of protein, the therapeutic effect of which is desired.

The object of the present invention is precisely to propose the use of specific chemical molecules for significantly increasing the efficiency of transfection of DNA with which they are combined.

More precisely, the present invention relates to a pharmaceutical composition, characterized in that it combines with at least one nucleic acid a tetrafunctional copolymer of formula (I):

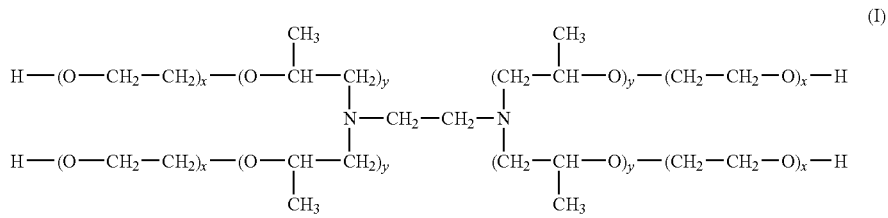

or one of its organic or mineral salts or derivatives, in which x and y represent, independently of one another, an integer of between 1 and 500 with x having a value such that said molecule comprises at least 30% by weight of ethylene oxide units, and in which the compound of formula (I) is preferably used in cationic form.

The abovementioned molecules, which are specific poloxamines, consist of hydrophobic segments (propylene oxide bearing the y indices), of hydrophilic segments (ethylene oxide bearing the x indices) and of a positively charged central ethylenediamine component ($NCH_2$—$CH_2N$).

The inventors have more particularly demonstrated that these poloxamines, which were until then presented as nonionic polymers (WO 00/47186), can in fact take a cationic form.

Surprisingly, the appearance of these positive charges on the central ethylenediamine component does not in any way harm the efficiency of cellular transfer, on the contrary. In fact, cationic chemical molecules of the cationic lipid, protein and cationic peptide type do not improve, with respect to naked DNA, gene transfer in muscle tissues (Lluis M. M. et al., 1999, Proc. Natl. Acad. Sci., vol. 96, pp. 4262-4267).

A particular subject of the invention is therefore a pharmaceutical composition, characterized in that it combines with at least one nucleic acid at least one organic or mineral salt of the tetrafunctional copolymer of formula (I):

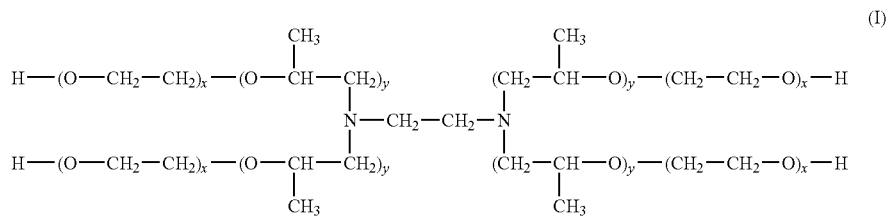

used in a cationic form, in which x and y represent, independently of one another, an integer of between 1 and 500 with x having a value such that said molecule comprises at least 30% by weight of ethylene oxide units.

The compound of general formula (I) is therefore preferably used in the form of one of its salts, and more preferably in a cationic form. To do this, the composition claimed combines with said compound a preferably mineral salt, and more preferably an alkali metal salt or an alkaline-earth metal salt. It may in particular be chosen from sodium chloride, potassium chloride or lithium chloride and sodium thiocyanate, or more preferably calcium chloride ($CaCl_2$) or magnesium chloride ($MgCl_2$).

This salt may be introduced in isotonic, hypotonic or hypertonic amount.

The inventors have also established the advantage of controlling the pH and/or the ionic composition of the formulation, in order to be sure that the copolymer of formula (I) is in its cationic form.

A pH of 6.5 to 8, preferably 7 to 7.8, more preferably 7.4, proves to be particularly advantageous.

According to a preferred embodiment of the invention, the composition is formulated in a medium referred to as Tyrode's (medium containing 3 mM $CaCl_2$, 2 mM $MgCl_2$, 6 mM KCl, 140 mM NaCl, 10 mM glucose and 10 mM Hepes, pH 7.4) (Tyrode Pharmacology. Philadelphia, 1908, 2nd edition, 1912). The presence of the Tyrode's makes it possible in particular to control the ionic composition of the formulation and the pH and, consequently, the use of the compound of formula (I) in a cationic form.

Without wishing to be bound to any mechanism of action, the inventors in fact observe that the poloxamines used in a cationic form, in particular in the presence of Tyrode medium, make it possible to condense the DNA.

Unexpectedly, the inventors have also demonstrated that the compounds of general formula (I), in which the ethylene oxide units are present in a proportion of at least 30% by weight, prove to be particularly efficient for the transfer of an associated gene in vivo. This efficiency is in particular illustrated by example 1 hereinafter. According to a preferred variant, the compounds according to the invention comprise no more than 85% by weight of ethylene oxide units. More preferably, they have approximately between 35 and 50%, and preferably approximately 40%, by weight of ethylene oxide units.

According to a preferred variant of the invention, the molecules of compounds of general formula (I) also have a molecular weight of at least 800 g/mol, and more preferably of between 1000 and 25 000 g/mol.

According to a preferred embodiment of the invention, the compounds of general formula have an EO/PO unit ratio of between 0.5 and 1.5, and preferably of the order of 1±0.2.

As compounds of general formula (I) that are most particularly suitable for the present invention, mention may more particularly be made of molecules having, respectively, a molecular weight of 1650 g for an EO/PO ratio of 15:16 (for example poloxamine 304), of 5500 g/mol for an EO/PO ratio of 50:56 (for example poloxamine 704) and of 6700 g/mol for an EO/PO ratio of 61:68 (for example poloxamine 904).

For the purpose of the present invention, the term "derivative" is intended to cover compounds which have the chemical structure of general formula I but which also carry secondary chemical or biological functions or entities capable of conferring on them complementary properties. Particularly representative of these derivatives are compounds of general formula I in which there is also as least one intra- or extracellular targeting unit. By way of nonlimiting illustration of these targeting units, mention may more particularly be made of peptides carrying a nuclear localization sequence, or peptides which recognize receptors present at the surface of certain cells.

According to a preferred embodiment, the composition is free of sodium phosphate and/or of glucose.

For the purpose of the present invention, the term "nucleic acid" covers both a deoxyribonucleic acid and a ribonucleic acid.

In this case, they may be sequences of natural or artificial origin, and in particular genomic DNA, cDNA, mRNA, tRNA, rRNA, small interference RNA (iRNA) hybrid sequences, or synthetic or semi-synthetic sequences of oligonucleotides which may or may not have been modified. These nucleic acids may be of human, animal, plant, bacterial, viral, etc. origin. They may be obtained by any technique known to those skilled in the art, and in particular by screening libraries, by chemical synthesis or by mixed methods including the chemical or enzymatic modification of sequences obtained by screening libraries. They may be chemically modified.

As regards more particularly the deoxyribonucleic acids, they may be single-stranded or double-stranded, just as short oligonucleotides or longer sequences. These deoxyribonucleic acids can carry therapeutic genes, regulatory sequences for transcription or for replication, modified or unmodified antisense sequences, regions for binding to other cellular components, etc. They may in particular direct the synthesis of a polypeptide specific for an infectious agent or may be capable of remedying a genetic or acquired deficiency.

For the purpose of the invention, the term "therapeutic gene" is intended to mean in particular any gene encoding a protein product having a therapeutic effect. The protein product thus encoded may be a protein, a peptide, etc. This protein product may be homologous with respect to the target cell (i.e. a product which is normally expressed in the target cell when said cell exhibits no pathology). In this case, the expression of a protein makes it possible, for example, to compensate for an insufficient expression in the cell or the expression of a protein that is inactive or weakly active due to a modification, or else to overexpress said protein. The therapeutic gene can also encode a mutant of a cellular protein, having increased stability, modified activity, etc. The protein product may also be heterologous with respect to the target cell. In this case, an expressed protein may, for example, add to or introduce a deficient activity in or into the cell, allowing it to combat a pathology or simulate an immune response.

Among the therapeutic products for the purpose of the present invention, mention may be made more particularly of enzymes, blood derivatives, hormones, lymphokines such as interleukins, interferons, TNF, etc., growth factors such as vascular endothelial growth factor, insulin-like growth factor and fibroblast growth factor, neurotransmitters or their precursors or enzymes for synthesizing them, trophic factors such as BDNF, CNTF, NGF, IGF, GMF, aFGF, bFGF, NT3, NT5 and HARP/pleiotrophin, dystrophin or a mini-dystrophin, utrophin, the cystic fibrosis-related CFTR protein, tumor suppressor genes such as p53, Rb, Rap1A, DCC and k-rev, genes encoding factors involved in clotting, such as factors VII, VIII and IX, genes involved in DNA repair, suicide genes (thymidine kinase, cytosine deaminase), genes for hemoglobin or other protein transporters, genes corresponding to the proteins involved in lipid metabolism, of apolipoprotein type chosen from apolipoproteins A-I, A-II, A-IV, B, C-I, C-II, C-III, D, E, F, G, H, J and Apo(A), metabolic enzymes such as, for example, lipoprotein lipase, hepatic lipase, lecithin cholesterol acyl-transferase, cholesterol 7-alpha-hydroxylase, phosphatidic acid phosphatase or lipid-transfer proteins such as cholesteryl ester transfer protein and phospholipid transfer protein, an HDL-binding protein or else a receptor chosen, for example, from LDL receptors, chylomicron-remnant receptors and scavenger receptors, erythropoietin, protein kinase C-3, etc.

The therapeutic nucleic acid may also be an antisense gene or sequence, the expression of which in the target cell makes it possible to control gene expression or cellular mRNA transcription. Such sequences may, for example, be transcribed, in the target cell, into RNAs that are complementary to cellular mRNAs, and thus block the translation thereof into protein. The therapeutic genes also comprise the sequences encoding ribozymes, which are capable of selectively destroying target RNAs.

As indicated above, the nucleic acid may also comprise one or more genes encoding an antigenic peptide capable of generating an immune response in humans or animals. In this particular embodiment, the invention therefore makes it possible to produce either vaccines or immuno-therapeutic treatments applied to humans or to animals, in particular against microorganisms, viruses or cancers. They may in particular be antigenic peptides specific for the Epstein Barr virus, for the HIV virus, for the hepatitis B virus, for the pseudorabies virus, for the syncitia forming virus or for other viruses, or else specific for tumors.

Preferably, the nucleic acid also comprises sequences which allow the expression of the therapeutic gene and/or of the gene encoding the antigenic peptide in the desired cell or organ. They may be the sequences which are naturally responsible for the expression of the gene under consideration when these sequences are capable of functioning in the infected cell. They may also be sequences of different origin (responsible for the expression of other proteins, or even synthetic sequences). In particular, they may be promoter sequences for eukaryotic or viral genes. For example, they may be promoter sequences derived from the genome of the cell that it is desired to infect. Similarly, they may be promoter sequences derived from the genome of a virus. In this regard, mention may be made, for example, of the promoters of the E1A, MLP, CMV and RSV genes, and tissue-specific promoters such as myosin chain promoters, for example, etc. In addition, these expression sequences can be modified by the addition of activation sequences, regulatory sequences, etc. They may also involve an inducible or repressible promoter.

Moreover, the nucleic acid can also comprise, in particular upstream of the therapeutic gene, a signal sequence which directs the synthesized therapeutic product into the target cell's secretion pathways. This signal sequence may be the natural signal sequence of the therapeutic product, but it may also be any other functional signal sequence, or an artificial signal sequence. The nucleic acid can also comprise a signal sequence which directs the synthesized therapeutic product to a particular compartment of the cell.

Besides the compound of general formula (I), the claimed compositions can comprise one or more adjuvant(s), and in particular a surfactant.

By way of representation of these adjuvants, mention may more particularly be made of celluloses, such as carboxymethylcellulose or hydroxypropylcellulose, hyaluronate or alginate salts, pectins, polyethylene glycols, dextrans, polyvinylpyrrolidones, chitosans, polyvinyl alcohols, propylene glycols, polyvinyl acetates, lecithins, polylactic and polyhydroxybutyric acids, and poloxamers of the Pluronics® (PEO-PPO-PEO) and reverse Pluronics® (PPO-PEO-PPO) series.

The compositions according to the invention may also use one or more targeting elements for directing the nucleic acid complexes to receptors or ligands at the surface of the cell. By way of example, the composition of the present invention may comprise one or more antibodies directed against cell surface molecules, or else one or more membrane-receptor ligands such as insulin, transferrin, folic acid or any other growth factor, cytokines or vitamins. Advantageously, the composition can use modified or unmodified lectins in order to target specific polysaccharides at the surface of the cell or on the neighboring extracellular matrix. Proteins containing an RGD unit, peptides containing a tandem of RGD units, which may or may not be cyclic, and also polylysine peptides or ligand peptides, which may be natural or synthetic, can thus be used.

The compound of general formula (I) may be incorporated in a proportion of 0.005% to 15% by weight/volume of said composition, and more preferably between 0.01% and 10% by weight/volume.

The claimed compositions are obtained by mixing the nucleic acid under consideration with at least one compound of general formula (I) in a solution compatible with in vivo administration. By way of illustration, these compositions may be prepared using the following protocol: a solution containing the nucleic acid (in particular DNA) two-times concentrated in 300 mM NaCl or 2× (two-times concentrated) Tyrode's and a two-times more concentrated aqueous solution containing a compound of general formula (I) are mixed volume for volume. The entire mixture is stirred, preferably by means of a VORTEX.

It has thus been noted that the claimed compounds of general formula (I) make it possible to increase the amount of protein synthesized by the muscle by a factor ranging from 5 to 20, compared to naked DNA. Moreover, with the composition according to the invention, no expression of a transgene has been noted in cells in culture in vitro, using conventional cell culturing methods.

The pharmaceutical compositions of the invention preferably contain a vehicle that is pharmaceutically acceptable for an injectable formulation, in particular for injection directly into the desired organ or for topical administration, for example to the skin and/or mucous membranes. They may in particular be sterile isotonic solutions or dry, in particular lyophilized, compositions which, by means of the addition, according to the case, of sterilized water or of physiological saline, make it possible to constitute injectable solutes.

It is clear that the doses of nucleic acid used for the injection and also the number of administrations can be adjusted by means of various parameters, and in particular as a function of the method of administration under consideration, of the pathology involved, of the nature of the gene to be expressed or of the desired duration of treatment.

As regards more particularly the method of administration, it may involve either direct injection into the tissues or the circulatory system, or treatment of cells in culture followed by reimplantation in vivo by injection or graft.

The claimed composition proves to be particularly advantageous for internal administration.

For the purpose of the present invention, the term "internal administration" signifies that the claimed compositions are compatible with administration into the tissue of an organism, for example a muscle, intra-dermally or subcutaneously. Furthermore, topical, oral, pulmonary, nasal and mucosal, such as, for example, buccal, vaginal or rectal, administration may be used.

The compositions according to the invention are particularly advantageous from a therapeutic point of view.

Thus, the potential applications are in the field of gene therapy and in particular in the production by a muscle tissue of a protein of local or systemic therapeutic interest.

In fact, after gene transfer into the muscle, in the presence of at least one molecule of general formula (I), this organ can serve as a reservoir for the synthesis of heterologous proteins which will act either locally (angiogenic factor, etc.) or systemically (clotting factor, growth factor, insulin, etc.).

What is more, the claimed composition may make it possible to abolish the plateau effect obtained with naked DNA. Specifically, when the amount of DNA injected into the muscle increases, the transfection increases in a linear fashion up to a certain dose, and then the amount of protein expressed reaches a maximum. On the other hand, with formulations in accordance with the invention, the amount of protein expressed increases exponentially with the increase in the amount of DNA injected into the muscle.

Another application comes from the field of immunization. In this case, a DNA encoding a bacterial, viral or other antigen is injected into cells, preferably muscle cells. Insofar as the claimed compositions are particularly advantageous for increasing the amount of proteins synthesized by the transfected cells, it is possible, by virtue of this, to obtain higher concentrations of antibodies and of cytotoxic T lymphocytes.

A subject of the present invention is also the use of a compound of general formula I or of one of its organic or mineral salts, as a vector for the cellular transfer in vivo of at least one nucleic acid as defined according to the invention.

The use of a compound of general formula I as defined above, for preparing a composition intended to provide the cellular transfer in vivo of at least one nucleic acid, is also within the scope of the invention.

The invention also relates to a method for the cellular transfection in vivo of at least one nucleic acid, characterized in that said nucleic acid is administered together with at least one compound of general formula I as defined above or one of its organic or mineral salts.

The administration can be carried out topically, directly into the cells under consideration, or by means of one of the routes of administration discussed above.

According to a preferred variant of the invention, the target cells are muscle cells or cardiac cells.

According to a preferred embodiment of the invention, poloxamine 304 is used as a vector for transferring a nucleic acid, in vivo, into muscle, or especially cardiac, cells.

Advantageously, the poloxamine 304 is formulated in a composition containing Tyrode's medium.

The present invention will be described more fully by means of the examples and figures which follow, which should be considered as nonlimiting illustrations.

FIGURES

FIG. 1: Expression of luciferase after intramuscular injection of DNA formulated according to the invention.

Figure 2:
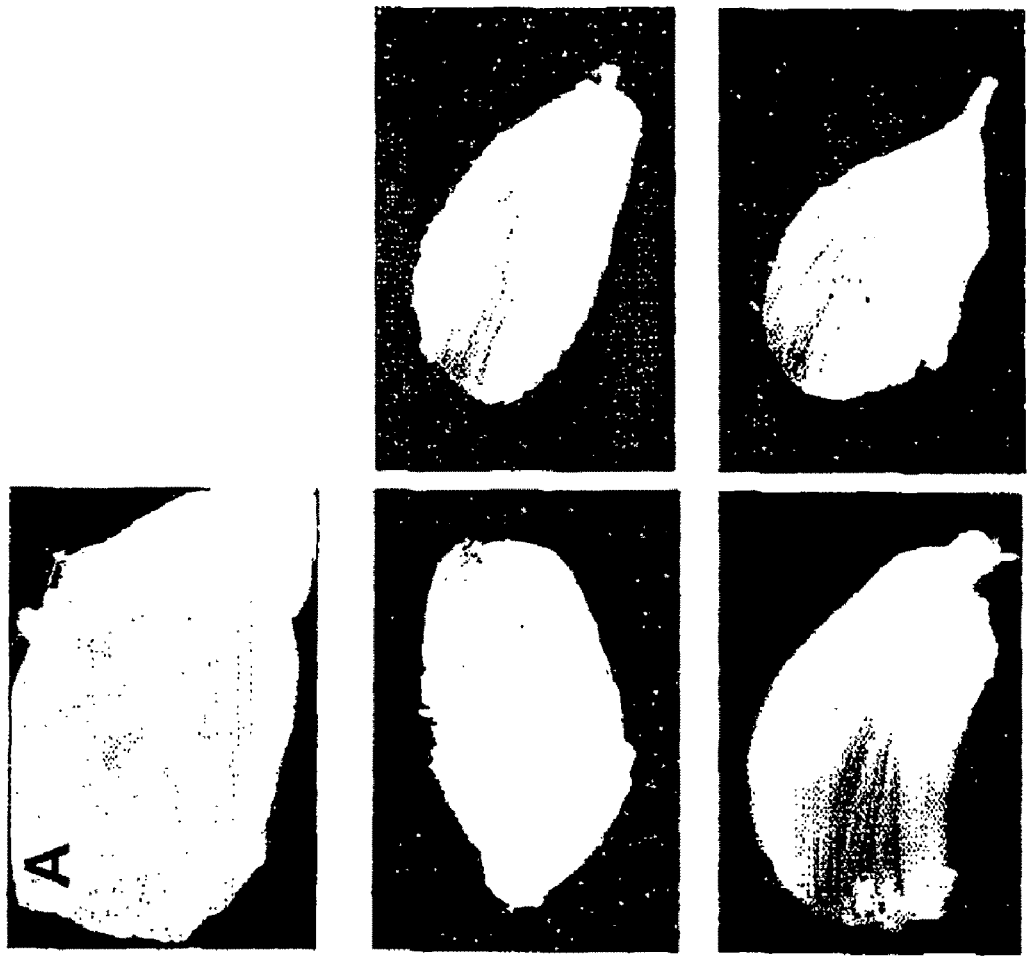

FIG. 2: Macroscopic visualization of β-galactosidase activity after injection, into the mouse anterior tibialis, of DNA formulated according to the invention.

Figure 3:
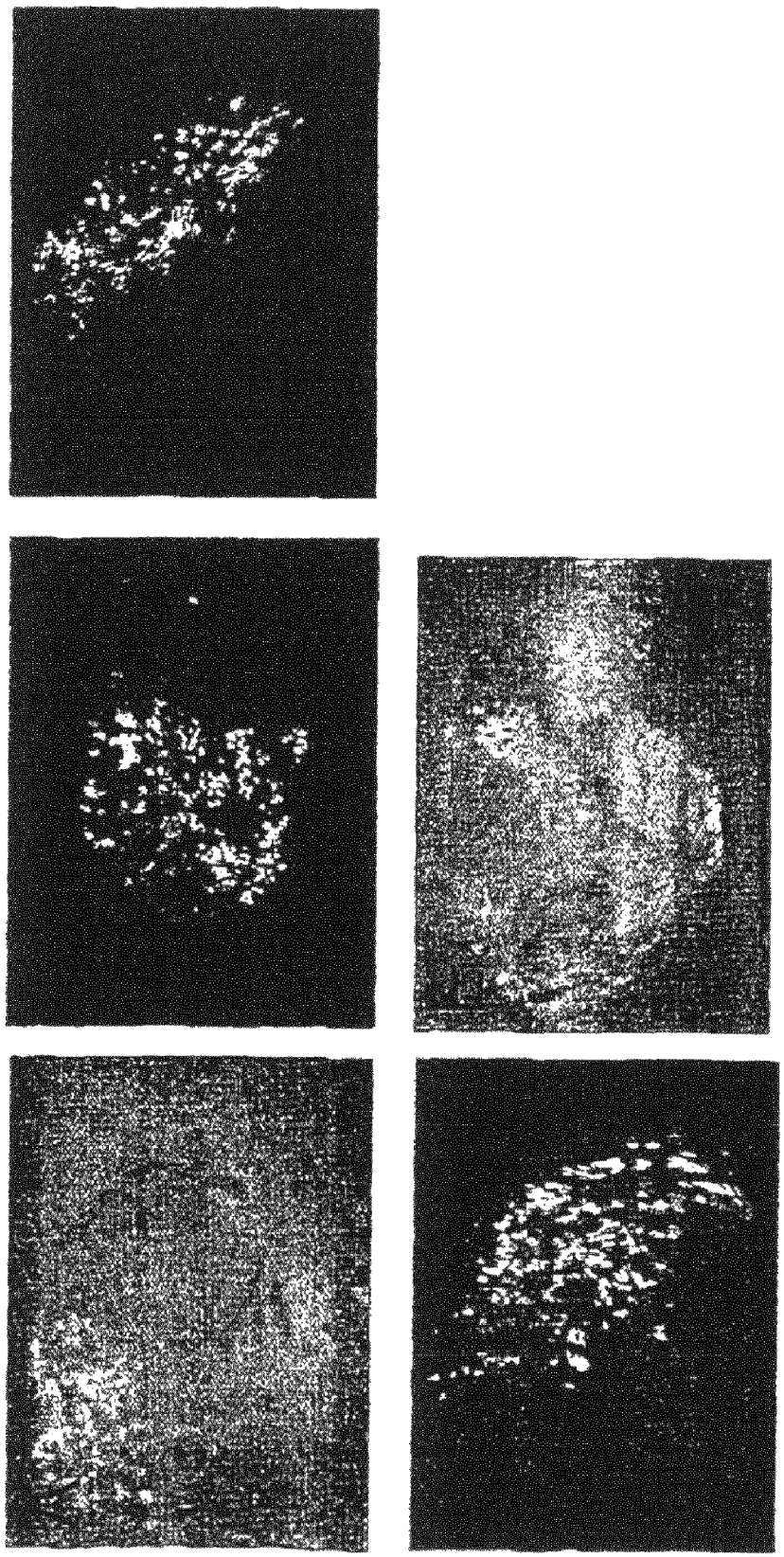

FIG. 3: Visualization by fluorescence microscopy of GFP expression in a muscle cell.

Figure 4:
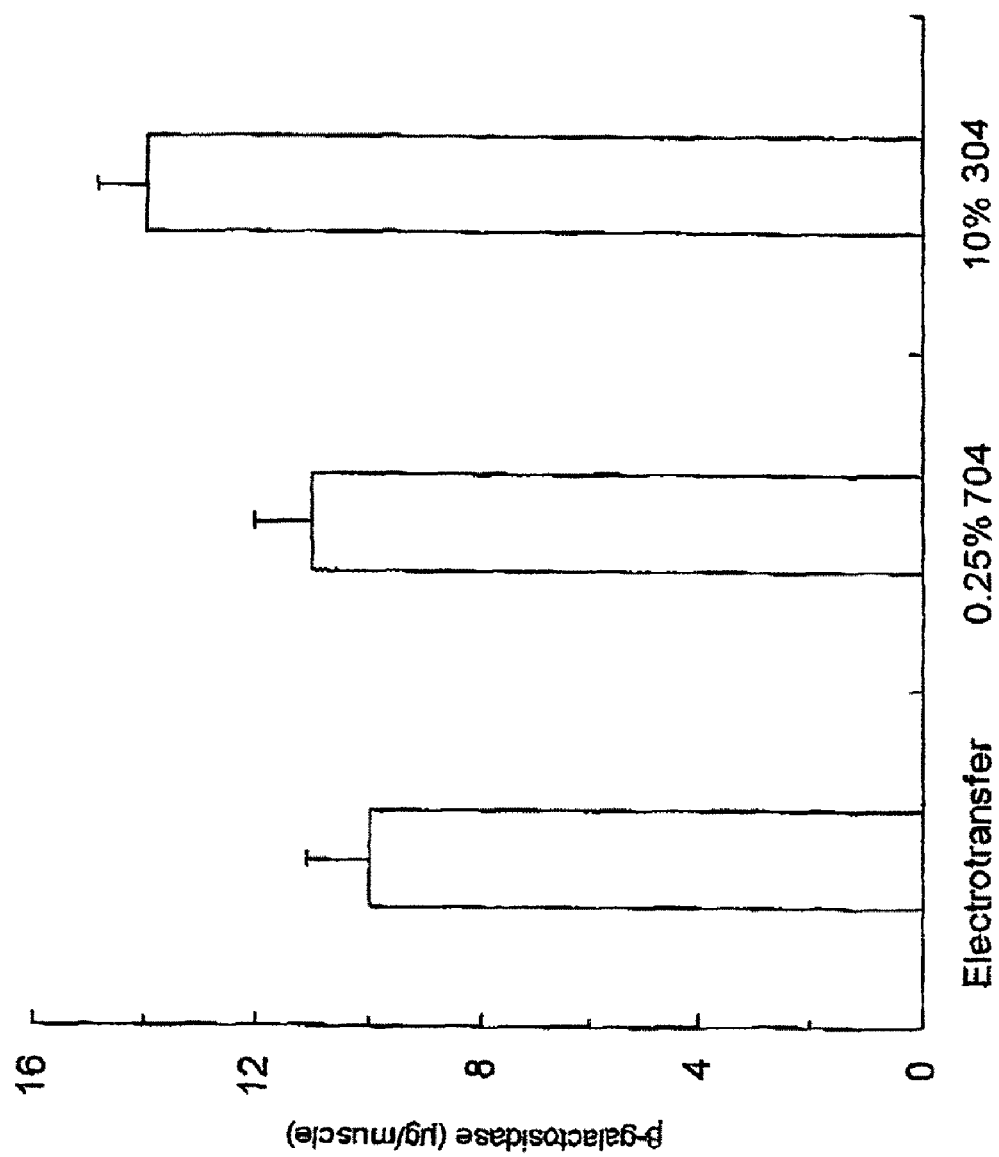

FIG. 4: Representation of β-galactosidase expression in the mouse anterior tibialis after injection, by electrotransfer, of said DNA or of said DNA formulated according to the invention.

FIG. 5: Visualization by cryoelectron microscopy. The 10% poloxamine 904 is mixed with DNA at 0.15 mg/ml, either in 150 mM NaCl (A, B) or in Tyrode's (140 mM NaCl, 6 mM KCl, 3 mM $CaCl_2$, 2 mM $MgCl_2$, 10 mM Hepes, pH 7.4, and 10 mM glucose) (C, D, E). Scale bar 100 nm.

MATERIALS

The compounds of general formula (I) tested are listed below in table 1, which records their physicochemical characteristics.

TABLE 1

| Poloxamine molecule | MW (g/mol) | % ethylene oxide | Number of ethylene oxides | Number of propylene oxides | EO/PO |
|---|---|---|---|---|---|
| 304 | 1650 | 40 | 15 | 16 | 0.93 |
| 704 | 5500 | 40 | 50 | 56 | 0.89 |
| 904 | 6700 | 40 | 61 | 68 | 0.89 |
| 908 | 25 000 | 80 | 454 | 85 | 5.3 |

EXAMPLE 1

In vivo Transfection of a Gene into the Muscle in the Presence of a Compound of General Formula (I)

Sample Preparation:

Two concentrations optimized for each of the products tested were considered.

Each trial uses 15 μg of DNA in 50 μl of 150 mM NaCl combined with two different concentrations for a compound of general formula (I) that is tested.

The concentrations tested are, for compound 904, respectively 0.01% and 0.1%, for compound 704: 0.25% and 0.5%, and for compound 304: 5% and 10%.

A control sample of DNA is formulated in the absence of compounds of general formula (I).

Each sample thus formulated is injected to the anterior tibialis of seven-week-old Swiss mice. After seven days, the mice are sacrificed and the injected anterior tibialis is dissected and then ground in a lysis buffer in the presence of a cocktail of protease inhibitors from Roche Diagnostics. The luciferase activity is assayed in the supernatant by luminometry (vector 2 from Perkin Elmer, Les Ulis, France) using the Luciferase Assay System® assay kit distributed by Promega (Charbonnières, France).

FIG. 1 reports the results obtained.

It is noted that the presence of a compound of general formula (I) makes it possible to significantly improve the expression of the luciferase activity by a factor ranging from 10 to 15.

EXAMPLE 2

Transfer of a Gene Encoding β-Galactosidase into a Skeletal Muscle

In the same way as in example 1, an injection of naked DNA (A), or of formulations in accordance with the invention containing 5% (B) or 10% of compound 304 (C), or 0.01% (D) and 0.1% of compound 904 (E) is given into the mouse anterior tibialis.

Seven days after the injections, expression of the β-galactosidase is observed by macroscopic visualization of the muscles which receive the formulations in accordance with the present invention. They exhibit regions of fibers expressing β-galactosidase and which become blue after revelation by immersing the muscles in a solution containing 2 mM of $MgCl_2$, potassium ferricyanide, potassium ferrocyanide, 5 mM of PBS, at pH 7, and in the presence of 1 mg/ml of 5-bromo-4-chloro-3-indolyl-β-d-galactopyranoside. The muscles are photographed 24 h after incubation in this solution at 37° C. The muscles which received only the naked DNA do not enable β-galactosidase expression to be visualized.

FIG. 2 illustrates these results.

EXAMPLE 3

Histological Analysis of the Expression of Green Fluorescent Protein (GFP) 7 Days after Injection of 50 μg of Naked DNA (A) or of 50 μg of DNA Formulated According to the Invention The formulations according to the invention that were tested are:

compound 304 at 5% (w/v) (B);
compound 704 at 0.25% (w/v) (C);
compound 904 at 0.1% (w/v) (D), and
compound 908 at $10^{-3}$% (w/v).

GFP expression is observed seven days after injection of the formulations, by observing a tissue section mounted between a slide and cover slip and then examined by fluorescence microscopy. FIG. 3 makes it possible to note that the number of muscle fibers expressing GFP is much greater when the DNA is formulated with 304 at 5% (B), 704 at 0.25% (C) and 904 at 0.1% (D). In the particular case of the DNA formulated with 908 at $10^{-3}$% (E), it is noted that the number of transfected fibers is equivalent to that obtained with the naked DNA.

The formulations in accordance with the present invention consequently allow a transfection that is at least as efficient as the naked DNA, or even clearly superior to it. These results confirm the advantage of the claimed formulations for the expression of a protein of local or systemic therapeutic interest.

EXAMPLE 4

Comparison of the Efficiency of Transfection into the Muscle of the Formulations in Accordance with the Present Invention, with Respect to Electrotransfer As regards the electrotransfer conditions, 50 μg of DNA encoding β-galactosidase were injected into the cranial labial muscle of 8-week-old Swiss mice, and the muscles then subjected to the conditions below. As regards the formulations, 50 μg of PCMV-βgal DNA were mixed with 304, 704 and 904 and then injected into the cranial libial muscles of the mice.

The electrotransfer technique is one of the only non-viral methods which makes it possible to improve in vivo transfection in the skeletal muscle.

The electrotransfer technique considered in the context of this comparative test consists in subjecting a muscle to an electric field of 200 V/cm with 8 pulses of 20 ms at a frequency of 2 Hz. This test is validated through expression of the β-galactosidase in the muscle.

FIG. 4 gives the results obtained. It is noted that the injection of naked DNA into the muscle subjected to the electrotransfer makes it possible to obtain, 7 days after the injection, 10 μg of β-galactosidase synthesized by the muscle. The formulations of DNA with 304 at 10% (w/v) and of DNA with 704 at 0.25% (w/v) make it possible to obtain the synthesis, respectively, of 14 and 11 μg of β-galactosidase/muscle.

The formulations of the present invention make it possible to obtain at least the same transfection efficiency as, or even greater efficiency than, that of the electrotransferred DNA. What is more, the present invention has the clear advantage of not requiring any specific equipment and of being much simpler to carry out since it is sufficient to mix compound (I) with the plasmid DNA. Finally, it is important to emphasize that electrotransfer cannot be applied for gene transfer into cardiac muscle, unlike the formulations in accordance with the present invention.

Electrotransfer is, in addition, a painful technique and requires regional if not general anesthesia.

EXAMPLE 5

Morphology, Visualized by Cryoelectron Microscopy, of The Poloxamine/DNA Particles as a Function of the Formulation Medium Poloxamine 904/DNA particles were formulated either with NaCl (150 mM) or with Tyrode's (medium containing 3 mM $CaCl_2$, 2 mM $MgCl_2$, 6 mM KCl, 140 mM NaCl, 10 mM glucose and 10 mM Hepes, pH 7.4).

For example, measurement of the zeta potential of the poloxamine 904 in the Tyrode's indicates a value of +9.5 mV, which reflects the cationic use of the poloxamine when it is combined with the DNA in the presence of Tyrode's.

The morphology of the particles was then visualized by cryoelectron microscopy. FIG. 5 reports the visualization.

When formulated with NaCl (150 mM), the DNA molecules aggregate with one another in the presence of poloxamines 904 to form large structures that are quite "loose", whereas, with Tyrode's, the DNA molecules form small spherical particles with the poloxamines 904 (FIGS. 5C, D and E). The same observation can be made with poloxamine 304.

Thus, by controlling the pH and the ionic composition of the medium, and in particular the presence of $CaCl_2$, small spherical particles are generated and would probably have an increased capacity for diffusion in the tissues.

EXAMPLE 6

Influence of the Formulation Medium on the Transfection Efficiency of the Poloxamine/DNA Formulations in NaCl or Tyrode's 50 μl of formulations containing 15 μg of plasmid DNA encoding luciferase are injected into the anterior tibialis in 8-week-old Swiss mice. The muscles are removed 7 days later and ground, and the luciferase activity is assayed.

The table below shows the amount of protein produced by the skeletal muscle is clearly greater when the formulations are carried out in Tyrode's.

| Poloxamine | Formulation medium | Luciferase (ng/muscle) |
|---|---|---|
| 704.05% (w/v) | NaCl | 94 |
| 704.05% (w/v) | Tyrode's | 625 |
| 904.0.01% (w/v) | NaCl | 74 |
| 904.0.01% (w/v) | Tyrode's | 971 |
| 904.01% (w/v) | NaCl | 78 |
| 904.01% (w/v) | Tyrode's | 519 |

EXAMPLE 7

In Vivo Transfer into the Heart of a Gene Encoding β-Galactosidase, in the Presence of a Compound of General Formula (I)

Sample Preparation:

Each trial uses 200 μg of plasmid DNA containing the gene encoding β-galactosidase, and a polymer in 700 μl of Tyrode's.

The polymers PE 6400, for the control sample, and poloxamines 304, 704 and 904 were tested at the concentrations (in weight/volume) of 0.5%, 2.5%, 0.75% and 0.1%, respectively.

Each sample thus formulated is injected into the pericardial sac of adult rats weighing approximately 200 g, after having crossed the diaphragm. The hearts are removed 7 days after the injection and are analyzed by histology in order to reveal the β-galactosidase activity. Only the poloxamine-based formulations make it possible to transfect cardiomyocytes in the left ventricle, and in particular poloxamine 304, which gives the best results. With poloxamine 304, it was observed that cardiomyocytes expressing β-galactosidase and therefore stained blue were present to a depth of up to ⅔ in the ventricular mass, which shows their considerable diffusion capacity.

The invention claimed is:

1. A lyophilized form of a pharmaceutically acceptable injectable composition, the pharmaceutically acceptable injectable composition comprising:
at least one nucleic acid;
a Tyrode's medium comprising:
140 mM NaCl,
6 mM KCl,
3 mM CaCl$_2$,
2 mM MgCl$_2$,
10 mM Hepes, pH 7.4, and
10 mM glucose; and
a tetrafunctional copolymer of formula (I):

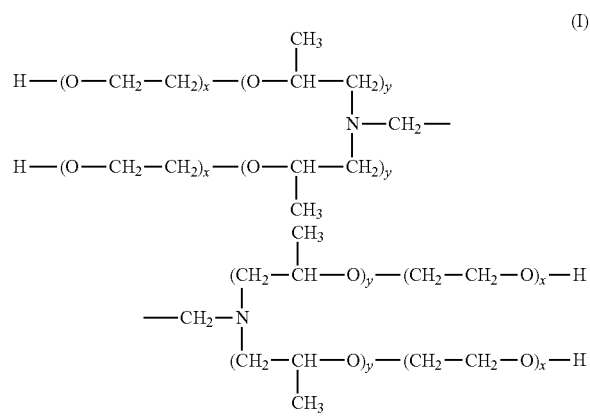

where:
x and y represent, independently of one another, an integer of between 1 and 500, and
the tetrafunctional copolymer is in a form of a mineral salt wherein said tetrafunctional copolymer is in a cationic form;
wherein the compound of formula (I) has a molecular weight of between 1,000 and 25,000 g/mol and an EO/PO ratio of 0.8 to 1.2.

2. The composition of claim 1, wherein the compound of formula (I) is present in a proportion of 0.005% to 15% by weight/volume.

3. The composition of claim 1, in which the compound of formula (I) is present in a proportion of 0.01% to 10% by weight/volume.

4. The composition of claim 1, wherein the compound of formula (I) further comprises at least one intra- or extracellular targeting unit.

5. The composition of claim 1, wherein the nucleic acid is a deoxyribonucleic acid.

6. The composition of claim 1, wherein the nucleic acid is a ribo-nucleic acid.

7. The composition of claim 1, wherein the nucleic acid is chemically modified.

8. The composition of claim 1, wherein the nucleic acid comprises an antisense sequence.

9. The composition of claim 1, wherein the nucleic acid is an interfering RNA.

10. The composition of claim 1, wherein the nucleic acid comprises a therapeutic gene.

* * * * *